(12) United States Patent
Ognibene et al.

(10) Patent No.: US 8,956,534 B2
(45) Date of Patent: Feb. 17, 2015

(54) PASSIVE COLUMN PRE-HEATER WITH SAMPLE BAND SPREADING REDUCTION FEATURE

(75) Inventors: Edward J. Ognibene, Belmont, MA (US); Joseph A. Kareh, Westwood, MA (US); Uwe D. Neue, Ashland, MA (US); Theodore D. Ciolkosz, Milton, MA (US); Richard W. Andrews, Rehoboth, MA (US); Marc Lemelin, Whitinsville, MA (US); Peyton C. Beals, Wrentham, MA (US)

(73) Assignee: Waters Technologies Corporation, Milford, MA (US)

( * ) Notice: Subject to any disclaimer, the term of this patent is extended or adjusted under 35 U.S.C. 154(b) by 1920 days.

(21) Appl. No.: 11/631,730

(22) PCT Filed: Aug. 5, 2005

(86) PCT No.: PCT/US2005/028081
§ 371 (c)(1),
(2), (4) Date: Oct. 9, 2008

(87) PCT Pub. No.: WO2006/017820
PCT Pub. Date: Feb. 16, 2006

(65) Prior Publication Data
US 2009/0211978 A1    Aug. 27, 2009

Related U.S. Application Data

(60) Provisional application No. 60/599,622, filed on Aug. 7, 2004.

(51) Int. Cl.
*G01N 30/30* (2006.01)
*B01D 15/20* (2006.01)
(Continued)

(52) U.S. Cl.
CPC ............. *B01D 15/161* (2013.01); *B01D 15/20* (2013.01); *G01N 2030/3046* (2013.01); *B01D 15/12* (2013.01); *G01N 30/30* (2013.01)
USPC .......................... 210/198.2; 210/656; 210/181

(58) Field of Classification Search
CPC ...... B01D 15/12; B01D 15/161; B01D 15/20; G01N 30/30; G01N 2030/3046
USPC ....................................... 210/198.2, 656, 181
See application file for complete search history.

(56) References Cited

U.S. PATENT DOCUMENTS 3,522,725 A * 8/1970 Waters .......................... 73/61.57
4,484,061 A   11/1984 Zelinka et al.
(Continued)

FOREIGN PATENT DOCUMENTS

JP   57-155277   9/1982
JP   60-058552   4/1985
(Continued)

OTHER PUBLICATIONS

PTO 10-3988 translation of Japan Patent No. 3030278.*
(Continued)

*Primary Examiner* — Ernest G Therkorn
(74) *Attorney, Agent, or Firm* — Edwards Wildman Palmer LLP; Scott D. Wofsy; George N. Chaclas

(57) ABSTRACT

Disclosed is a chromatographic system and method which includes a passive pre-heater assembly. In the inventive system and method a fluid mixture is supplied from an injector to the pre-heater assembly and then to a chromatographic column having an active heating source. The pre-heater assembly includes a convoluted tube with first and second ends and a fluid passage extending centrally therebetween, first and second end fittings attached respectively to the first and second ends of the convoluted tube, and a thermally conductive film attached to an outer surface of the convoluted tube. The first end fitting is adapted for fluidly connecting the first end of the convoluted tube to the injector and the second end fitting is adapted for fluidly connecting the second end of the convoluted tube to the chromatographic column. The thermally conductive film conveys heat from an active heating source of a chromatographic column to the convoluted tube when the pre-heater assembly is positioned adjacent to the active heating source. The central fluid passage in the convoluted tube has a series of bends which function to create a secondary fluid flow field that is substantially orthogonal to a primary flow field established when fluid is traversing the fluid passage in the tube.

8 Claims, 7 Drawing Sheets

(51) Int. Cl.
  *B01D 15/12*   (2006.01)
  *B01D 15/16*   (2006.01)

(56) References Cited

U.S. PATENT DOCUMENTS

| | | | |
|---|---|---|---|
| 4,726,822 | A | 2/1988 | Cates et al. |
| 4,966,695 | A * | 10/1990 | Joshua ................ 210/198.2 |
| 5,005,399 | A | 4/1991 | Holtzclaw et al. |
| 5,135,549 | A * | 8/1992 | Phillips et al. .............. 95/8 |
| 5,183,486 | A * | 2/1993 | Gatten et al. ............ 73/19.1 |
| 5,196,039 | A * | 3/1993 | Phillips et al. ............ 210/656 |
| 5,238,557 | A * | 8/1993 | Schneider et al. ....... 210/198.2 |
| 5,238,653 | A * | 8/1993 | Bourne ...................... 422/70 |
| 6,355,165 | B1 * | 3/2002 | Sutton et al. ........... 210/198.2 |
| 6,423,120 | B1 * | 7/2002 | Nickerson et al. ............ 95/87 |
| 6,568,244 | B2 * | 5/2003 | Binz et al. ................ 73/23.2 |
| 6,579,345 | B2 | 6/2003 | Munari et al. |
| 2002/0157951 | A1 * | 10/2002 | Foret et al. .............. 204/451 |

FOREIGN PATENT DOCUMENTS

| | | |
|---|---|---|
| JP | 62-115176 A | 7/1987 |
| JP | 2248857 | 10/1990 |
| JP | 03-030278 | 2/1991 |
| JP | 9251015 | 9/1997 |
| JP | 2000-111536 | 4/2000 |
| JP | 2001-017851 | 1/2001 |
| JP | 2007-525066 | 10/2009 |

OTHER PUBLICATIONS

PTO 10-3987 translation of Japan Patent No. 57155277.*
PTO 10-3986 translation of Japan Patent No. 2001017851.*
PTO 10-3992 translation of Japan Patent No. 2000-111536.*
PTO 10-3984 translation of Japan Patent No. 60058552.*
Office Action from corresponding Japanese Patent Application No. 2007-525066 dated Sep. 6, 2011.
Balejova, et al., "Heat Transfer for Laminar Flow in Curved Pipes with Uniform Wall Heat Flux," Acta Technica CSAV, No. 2, pp. 183-195, 1977.
Dey, et al., "Second boundary layer and wall shear for fully developed flow in curved pipes," Proc. R. Soc. Lond. A 458, 283-298, (2002).
Dravid, et al., "Effect of Secondary Fluid Motion on Laminar Flow Heat Transfer in Helically Coiled Tubes," AIChE Journal (vol. 17, No. 5), pp. 1114-1122, Sep. 1971.

* cited by examiner

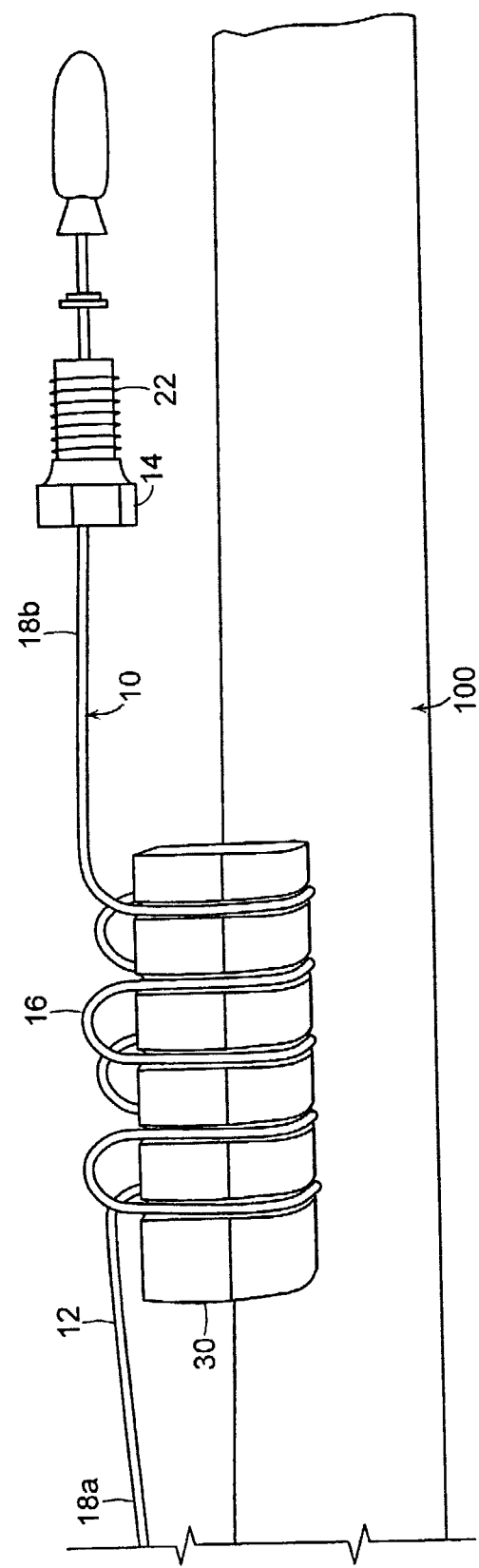

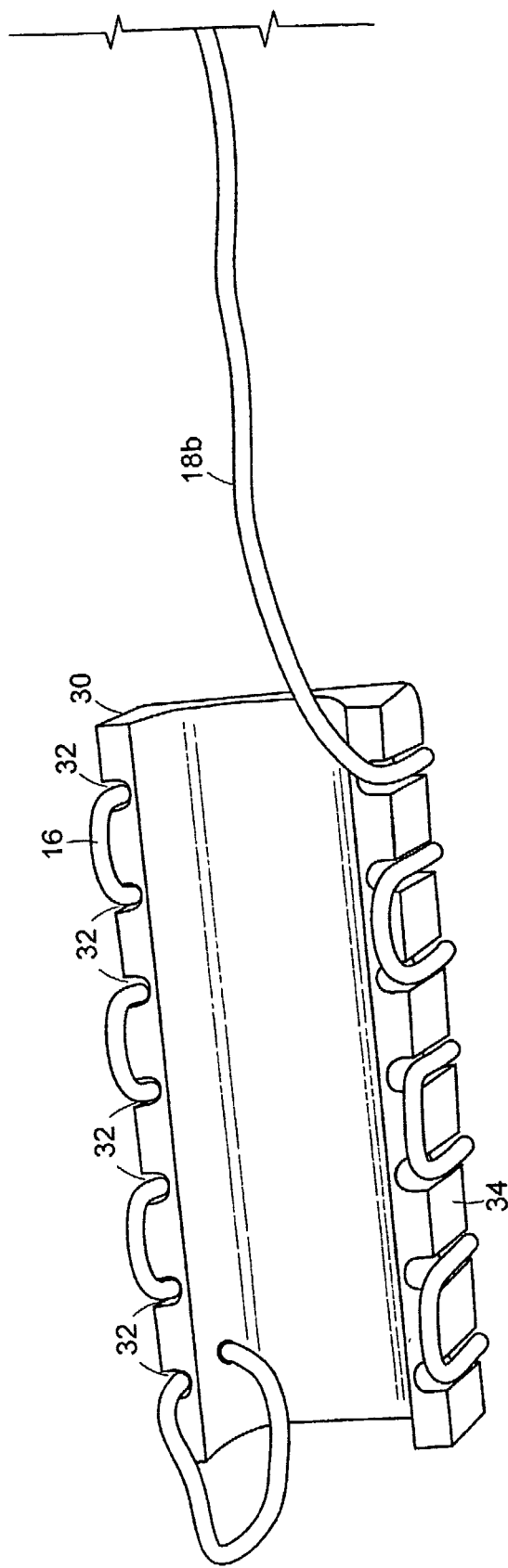

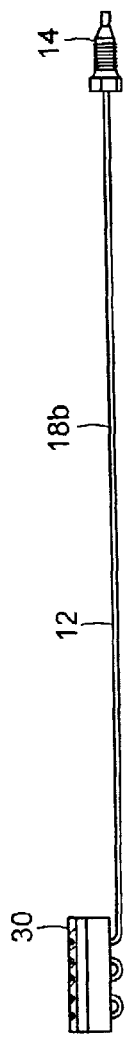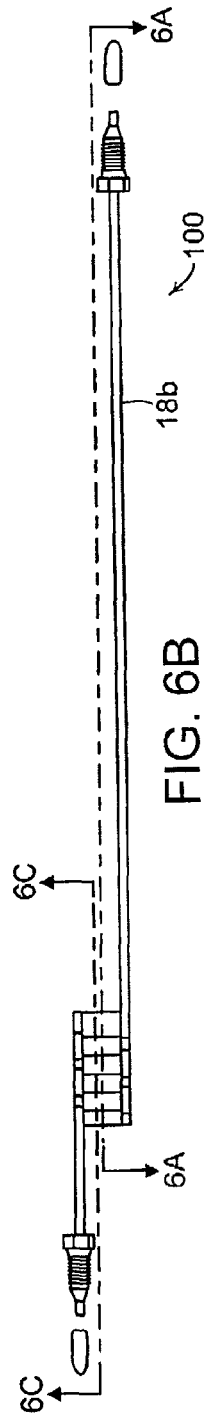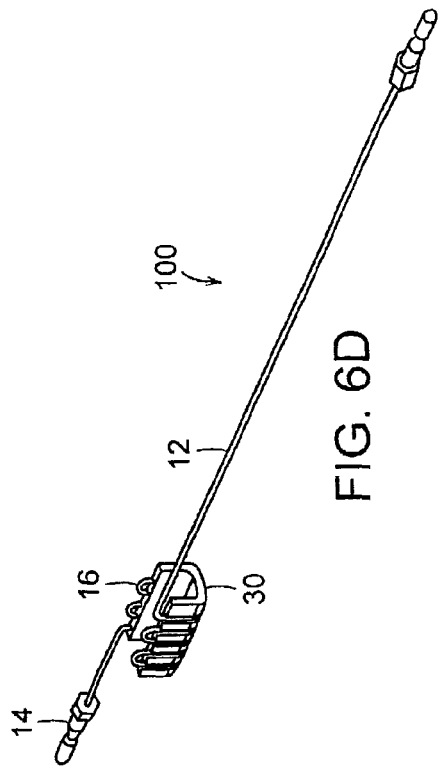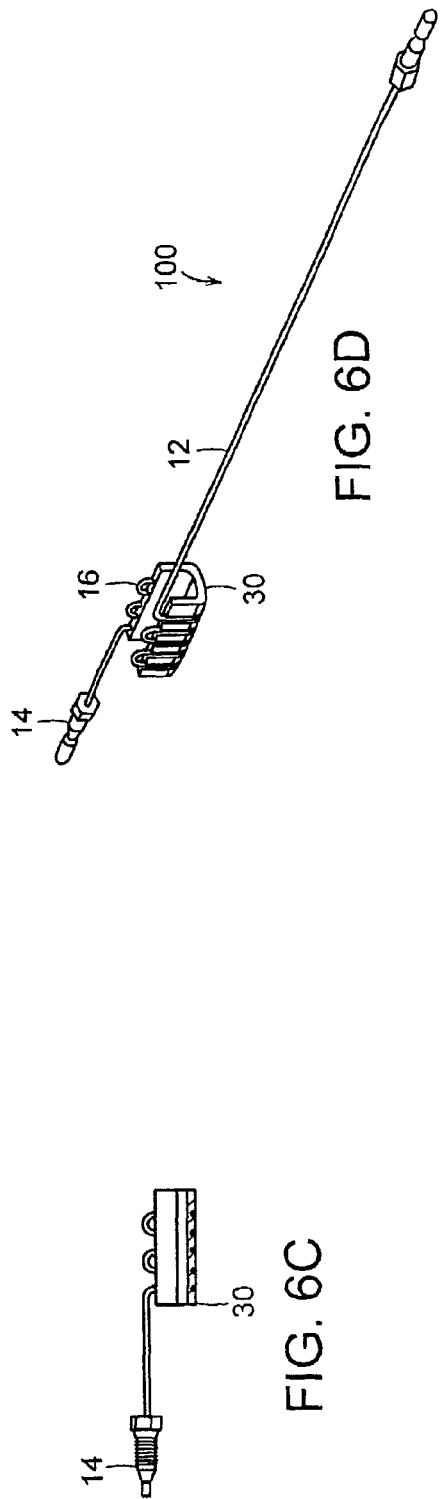

PASSIVE COLUMN PRE-HEATER WITH SAMPLE BAND SPREADING REDUCTION FEATURE

This application is a U.S. national phase application, pursuant to 35 U.S.C. §371, of PCT international application Ser. No. PCT/2005/028081, filed Aug. 5, 2005, designating the United States and published in English on Feb. 16, 2006 as publication WO 2006/017820 A1, which claims priority to U.S. provisional application Ser. No. 60/599,622, filed Aug. 7, 2004. The entire contents of the aforementioned patent applications are incorporated herein by this reference.

RELATED APPLICATION

This application claims the benefit of U.S. Provisional Application No. 60/599,622 filed, Aug. 7, 2004, the entire contents of which are incorporated herein by reference.

BACKGROUND OF THE INVENTION

Chromatography is a process for separating mixtures by virtue of their differences in absorbency. FIG. 1 illustrates one embodiment of a typical chromatographic system. Although there are other types of chromatography (e.g., paper and thin layer), most modern applications include a mobile phase and a stationary phase and the separation of the fluid mixture takes place in a column.

The column is usually a glass or metal tube of sufficient strength to withstand the pressures that may be applied across it. The control over column temperature is critical to the resolving efficiency of the column, whether the system is designed to operate isothermally or by temperature programmed analysis. Such column temperature control can be achieved by heating of the column in a convection oven (as shown) or by resistance heating techniques.

The column can be, for example, a packed bed or open tubular column. The column contains the stationary phase of the process, i.e., the material for which the components to be separated have varying affinities. The mobile phase of the chromatographic process is comprised of a solvent or mixture of solvents into which the sample to be analyzed is injected. The mobile phase enters the column and the sample is absorbed onto the stationary phase. The solvent or solvent mixture is not absorbed on the stationary phase, but passes through the column.

As illustrated in FIG. 1, a first pump is used to draw a first solvent from a tank and supply it at a desired flow velocity and pressure to a T-shaped piping connector. A second pump is used to draw a second solvent from a second tank and supply it at a desired flow velocity and pressure to the T-shaped piping connector. At the T-shaped piping connector, the solvents are blended to achieve a solvent mixture having desired properties. The flow velocity of each solvent can be adjusted over time so as to vary the composition of the solvent mixture over time. A variation in the solvent mixture over time is called a solvent or compositional gradient.

A third pump is used to supply the sample or feed to a second T-shaped piping connection where it is injected into the solvent mixture and blended therewith, forming the mobile phase.

The mobile phase runs through the column and the sample is absorbed onto the stationary phase. As the sample flows through the column, its different components will adsorb to the stationary phase to varying degrees. Those with strong attraction to the support move more slowly than those with weak attraction. This difference in speed of movement is how the components are separated.

After the sample is flushed or displaced from the stationary phase, the different components will elute from the column at different times. The components with the least affinity for the stationary phase will elute first, while those with the greatest affinity for the stationary phase will elute last. A detector analyses the emerging stream by measuring a property, which is related to concentration and characteristic of chemical composition. For example, the refractive index or ultra-violet absorbance is measured.

A disadvantage associated with the system disclosed in FIG. 1 is that temperature of the fluid mixture or mobile phase provided to the column and column heater is not always constant, especially in long (multi-hour) chromatographic runs where room temperature swings are non-trivial. These temperature gradients can adversely impact the accuracy of the chromatographic analysis.

In view of the above, there is a need for a device for use with a chromatographic system, which pre-heats the sample before it is injected into the column and provides a tighter level of column heater sensitivity by minimizing the column inlet fluid temperature fluctuations. Still further, there is a need for a device that passively (i.e., without requiring a separate heating element and control system) pre-heats the mobile phase prior to its entry into the column and reduces sample band spreading or dispersion.

SUMMARY OF THE INVENTION

The subject invention relates to chromatography systems and, more particularly, to an assembly for use in a chromatographic system, which passively pre-heats the fluid sample provided to the column and reduces sample band spreading or dispersion. Thus, in one aspect, the invention provides a passive pre-heater assembly for use in a chromatographic system in which a fluid mixture is supplied from an injector to a chromatographic column having an active heating source. The pre-heater assembly includes, inter alia, a convoluted tube with first and second ends and a fluid passage extending centrally therebetween, first and second end fittings attached respectively to the first and second ends of the convoluted tube, and a thermally conductive film attached to an outer surface of the convoluted tube. The first end flitting is adapted for fluidly connecting the first end of the convoluted tube to the injector and the second end fitting is adapted for fluidly connecting the second end of the convoluted tube to the chromatographic column. The thermally conductive film conveys heat from an active heating source of a chromatographic column to the convoluted tube when the pre-heater assembly is positioned adjacent to the active heating source. Preferably, the convoluted tube is made from a soft, thermally conductive metal, but other thermally conductive materials, such as Teflon, can be selected depending on the application and fluid pressure requirements.

Those skilled in the art will readily appreciate that the present invention can be operative without the thermally conductive film. Still further, other means for improving the thermal conductivity between the convoluted tube and the active heat source can be used. For example, a thermally conductive coating or film can be applied to the tube by chemical vapor deposition or physical vapor deposition.

It is envisioned that in alternative embodiments the pre-heater assembly further includes a support element which has at least one channel formed in its exterior surface that receives the convoluted tube. The support element preferably has a U-shaped axial cross section that is adapted for being inserted into a column tray. Preferably, the support element is made from aluminum, but other thermally conductive materials can be used.

The central fluid passage in the convoluted tube has a series of bends which are adapted and configured to create a secondary fluid flow field that is substantially orthogonal to a primary flow field established when fluid is traversing the fluid passage. As will be described herein below, the creation of the secondary flow field produces a net reduction in fluid sample band spreading or dispersion.

The invention further provides a passive pre-heater assembly for use in a chromatographic system in which a fluid mixture is supplied from an injector to a chromatographic column which has an active heating source.

The pre-heater assembly includes, among other elements, a convoluted tube which has first and second ends and a fluid passage extending centrally therebetween, a support element which has at least one channel formed in an exterior surface thereof which receives the convoluted tube, and a thermally conductive film attached to the exterior surface of the support element. The convoluted tube preferably has a series of bends which create a secondary fluid flow field that is substantially orthogonal to a primary flow field established when fluid is traversing the fluid passage.

The thermally conductive film conveys heat from an active heating source of a chromatographic column to the support element and convoluted tube when the pre-heater assembly is positioned adjacent to an active heating source for the chromatographic column.

The pre-heater assembly further includes means associated with the first and second ends of the convoluted tube for fluidly connecting the first end of the convoluted tube to an injector and for fluidly connecting the second end of the convoluted tube to a chromatographic column. For example, the means for connecting the convoluted tube can include threaded end fittings or quick disconnects.

The invention filter provides a chromatographic system which includes, inter alia, a fluid injector for supplying a fluid mixture at a desired pressure and velocity, a pre-heater assembly for receiving the fluid mixture from the fluid injector, a chromatographic column adapted and configured for receiving the fluid mixture from the pre-heater assembly and adsorbing a portion thereof, and an active heating source in direct contact with the chromatographic column for heating the fluid contained in the column. The pre-heater assembly is in the novel chromatographic system can be constructed as described above.

The invention is still further directed to a chromatographic method which includes, among other steps, the steps of:

a) providing a fluid injector for supplying a fluid mixture at a desired pressure and velocity;

b) fluidly attaching a first end of a pre-heater assembly to the injector, the pre-heater assembly adapted for receiving the fluid mixture from the fluid injector and passively providing heat thereto;

c) fluidly attaching a chromatographic column to a second end of the pre-heater assembly, the column being adapted and configured for receiving the pre-heated fluid mixture from the pre-heater assembly and adsorbing a portion thereof;

d) providing an active heating source in direct contact with the chromatographic column for heating the fluid contained in the column; and e) positioning the pre-heater assembly adjacent to the active heating source such that the fluid mixture provided to the pre-heater assembly is heated thereby.

It is envisioned that the inventive method can further include the step of attaching a thermally conductive film to an outer surface of the convoluted tube and adjacent to the active heating source. The film conveys heat from the active heating source of the chromatographic column to the convoluted tube.

Additionally, the method can also include the step of providing a support element for the pre-heater assembly which has at least one channel formed in an exterior surface thereof and is adapted for receiving the convoluted tube.

BRIEF DESCRIPTION OF THE DRAWINGS

So that those having ordinary skill in the art to which the disclosed system appertains will more readily understand how to make and use the same, reference may be had to the drawings wherein:

FIG. 3 is a photograph providing an elevational view of an embodiment of the passive pre-heater assembly of the present invention;

FIG. 4 is a photograph providing a top perspective view of the passive pre-heater assembly of FIG. 3;

FIG. 6 is a mechanical drawing which illustrates in elevational view, plan view, cross-sectional view and perspective view, a representative embodiment of the passive pre-heater assembly of the present invention.

These and other features of the passive pre-heater assembly of the present application will become more readily apparent to those having ordinary skill in the art from the following detailed description of the preferred embodiments.

DETAILED DESCRIPTION OF PREFERRED EMBODIMENTS

Figure 1:
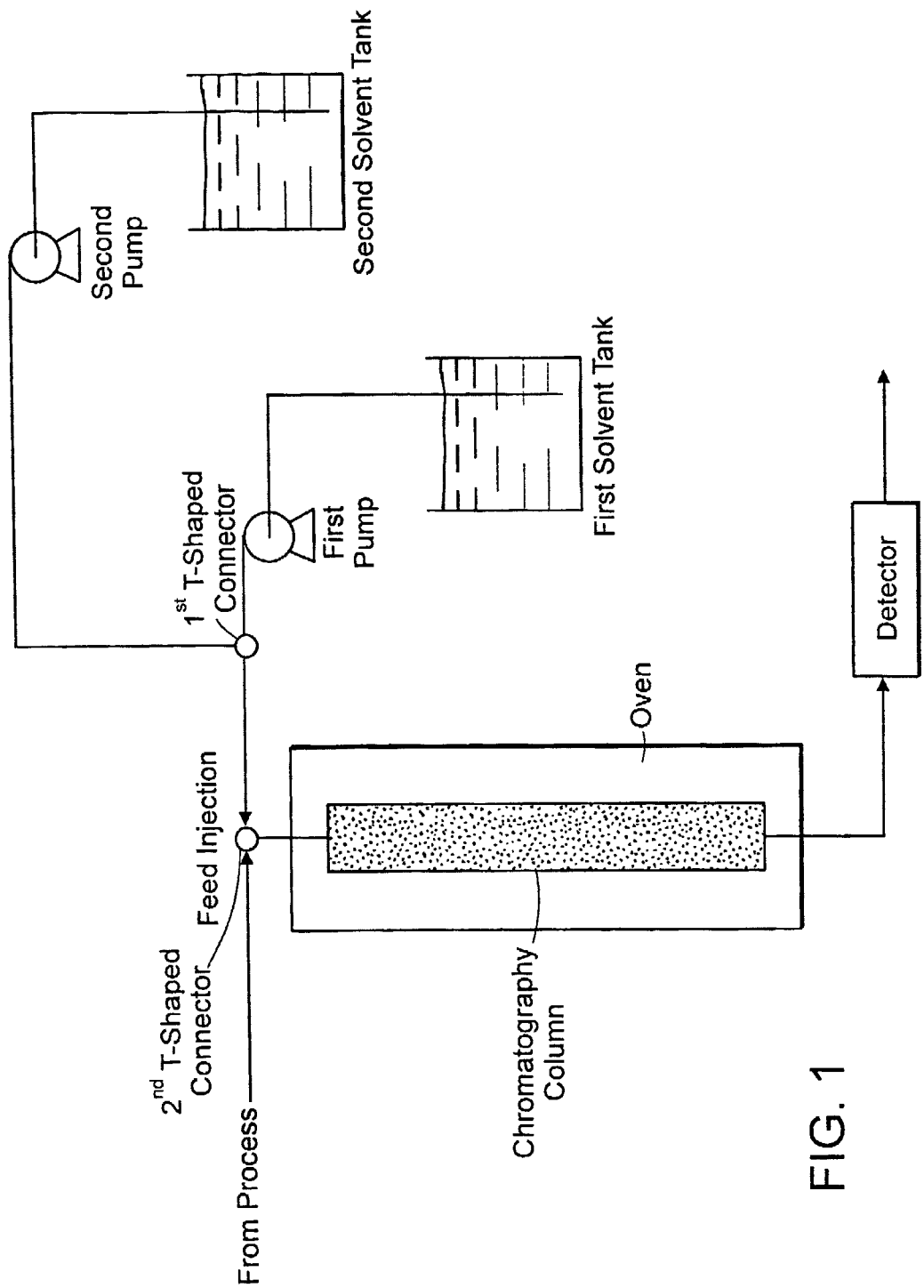
FIG. 1 is a schematic overview of a typical chromatographic system in which an embodiment of the present invention may be used.
Figure 2:
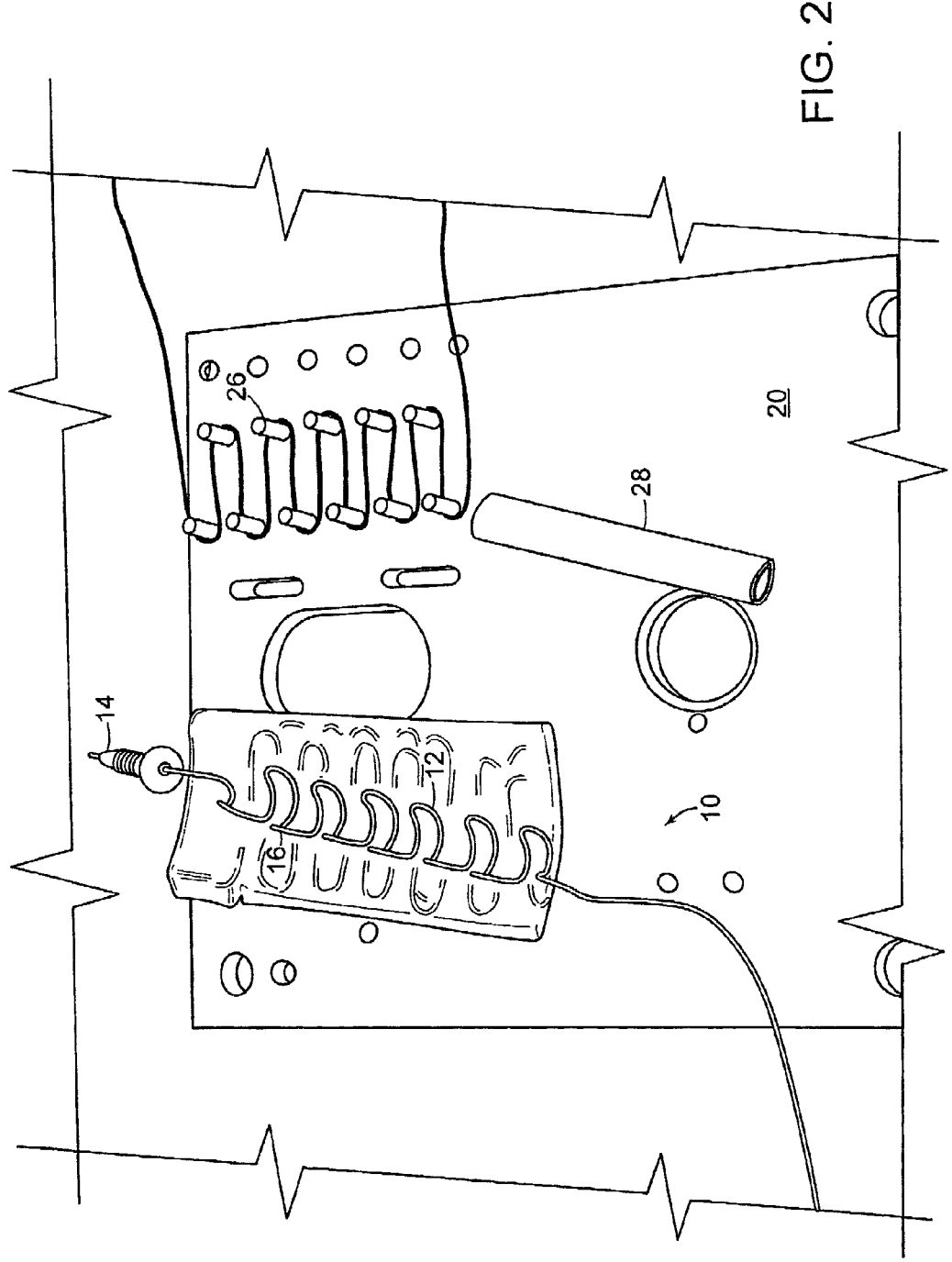
FIG. 2 is a photograph providing a top perspective view of an embodiment of the convoluted tube used in a passive pre-heater assembly of the present invention and an exemplary fabrication fixture.

Referring now to the drawings, there is illustrated in FIGS. 2 through 4, a tubing assembly constructed in accordance with an embodiment of the subject invention and designated by reference numeral 10. Tubing assembly 10 is adapted for use in passive column pre-heater assembly 100, as shown in FIGS. 5a through 5c and 6.

Tubing assembly 10 includes, inter alia, a tube 12 and first and second end fittings 14 (only one shown). Tube 12 has a convoluted portion 16, substantially straight end portions 18a and 18b, and a central-passage extending between the end portions 18a and 18b. Fittings 14 have been provided on each end 18a, 18b of the tube 12 to facilitate fluidly connecting pre-heater assembly 100 between an injector and a chromatographic column in a chromatographic system. As shown in FIG. 3, end fitting 14 has a series of male threads 22 formed on its exterior surface which are adapted for engaging with corresponding female threads provided on tubing or piping connectors emanating from an injector or leading to a chromatographic column tubing.

Referring now to FIG. 2, a portion of tube 12 has been convoluted or manipulated into a labyrinthine configuration by using fixture 20. The purpose for shaping tube 12 in this manner will be described in detail herein below. Fixture 20 primarily includes a steel plate 24 having two rows of studs 26 welded on its upper surface and a piece of cylindrical bar 28.

The studs 26 are equally spaced along two axial rows, but the studs in the second row are axially offset from the first row. The flexible tube 12 is bent around the studs 26 to form a planar labyrinth. Then the cylindrical bar 28 is used to bend the planar labyrinth into a three-dimensional convolution. Those skilled in the art will readily appreciate that a multitude of methods can be used to convolute a portion of tube 12 without departing from the inventive aspects of the present disclosure.

Pre-heater assembly 100 further includes a support element 30 which has a plurality of channels 32 formed in exterior surface 34 (FIG. 4). The convoluted portion 16 of tube 12 is positioned within the channels 32. The support element has a U-shaped axial cross section that is adapted for being inserted into a column tray 50 (see FIG. 5c). In this embodiment, the support element 30 is made from aluminum, but those skilled in the art will readily appreciate that other thermally conductive materials can be used.

Figure 5A:
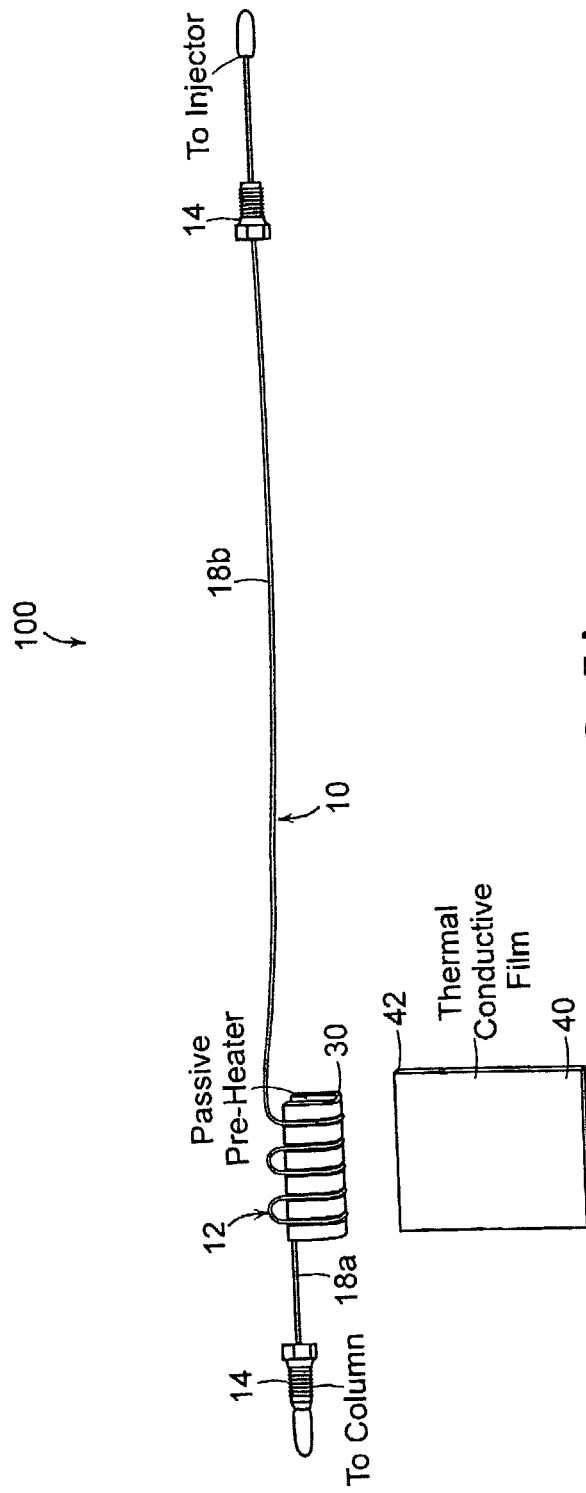
FIGS. 5A through 5C are photographs which illustrate a representative method for installing the passive pre-heater assembly of the present invention into a column heater tray of a chromatography system.

To improve the passive heat transfer capabilities of the pre-heater assembly 100, a thermally conductive film 40 is attached to an outer surface of the convoluted tube 12 and the support element 30 (FIG. 5a). The thermally conductive film 40 conveys heat from an active heating source (for example, a resistance heater) of a chromatographic column to the convoluted tube 12 when the pre-heater assembly 100 is positioned adjacent to the active heating source.

Figure 5B:
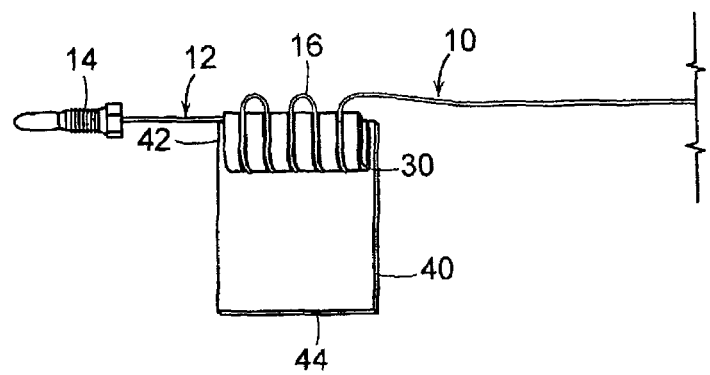
Figure 5C:
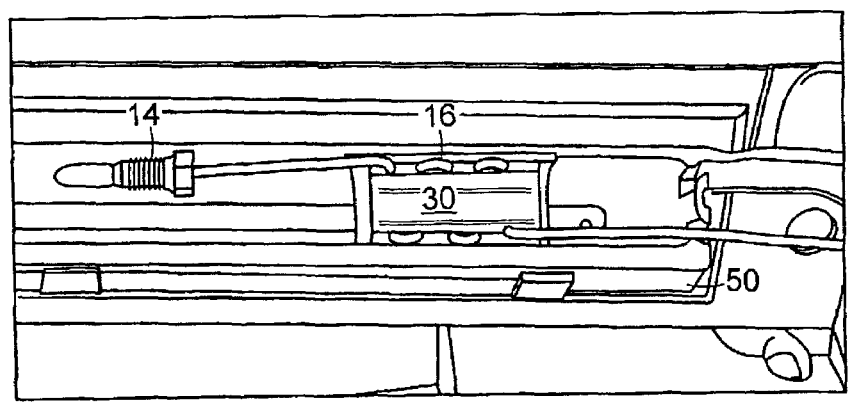

The procedure for installing the above-described embodiment of passive pre-heater assembly 100 into a chromatographic system is illustrated in FIGS. 5a through 5c and is summarized as follows:

1. Remove the plastic liners from the thermally conductive film 40.
2. Center the tube assembly 10 and support element 30 along the top edge 42 of the conductive film as shown in FIG. 5b.
3. Fold the thermally conductive film 40 around the passive pre-heater assembly 100.
4. While holding the film encased assembly by its upper and lower edges, 42 and 44 respectively, insert the assembly into column tray 50.
5. Connect end portion 18a of tube 12 to the "to column" port on the injector using end fitting 14.
6. Connect end portion 18b of tube 12 to the inlet end of the column. (Note: if a guard column is used, fold the tubing to position the guard column within the passive heater.

In the presently described embodiment, the pre-heater assembly is positioned in thermal contact with the column heater. Passive heating is achieved because the tube 12 and sample within the tube by virtue of their thermal coupling with the column heater are heated to the same "set" temperature of the column heater (i.e., the desired temperature of the column). Therefore, there is no separate control loop for the pre-heater assembly 100 and only the column heater is controlled using a feedback scheme.

The passive pre-heater assembly 100 provides for passive pre-heating of the fluid mixture (i.e., the sample) before it enters the column in combination with minimizing or reducing the band spreading or dispersion. The weaving, bending or convoluting of the tube assembly is such that it has a series of tight bends that stimulate secondary flow in the primary fluid flow stream. Furthermore, the bends are produced in such a manner as to create a net reduction in sample band spreading/dispersion by using the secondary flow field to shape and manage the sample as it passes through the tubing assembly. More specifically, the bending of the tube in three dimensions sets up secondary flow that helps maintain sample bolus as it bases through the tube. The degree of band spreading is generally directly proportional to the tube length for straight tubes. This three-dimensional weaving or convolution tends to reduce band spreading through secondary flow. Tubes with the appropriate convoluted structure will exhibit less band spreading than the equivalent length of straight tubing, and may even offer less band spreading than longer tubes.

While the invention has been described with respect to preferred embodiments, those skilled in the art will readily appreciate that various changes and/or modifications can be made to the invention without departing from the spirit or scope of the invention as defined by the appended claims.

INCORPORATION BY REFERENCE

All patents, published patent applications and other references disclosed herein are hereby expressly incorporated herein in their entireties by reference.

EQUIVALENTS

Although the subject invention has been described with respect to preferred embodiments, those skilled in the art will readily appreciate that various changes and/or modifications can be made to the invention without departing from the spirit or scope of the invention.

What is claimed is:
1. A chromatographic system comprising:
a) a fluid injector for supplying a fluid mixture at a desired pressure and velocity;
b) a pre-heater assembly for receiving the fluid mixture from the fluid injector, the pre-heater assembly including:
   i) an elongated tube having first and second ends and a fluid passage extending centrally therebetween, the tube being formed so as to have a plurality of convolutions arranged such that a successive convolution is axially offset from a previous convolution such that the plurality of convolutions stimulates secondary flows in a primary fluid flow stream; and
   ii) first and second end fittings attached respectively to the first and second ends of the tube, the first end fitting being adapted for fluidly connecting the first end of the convoluted tube to the fluid injector and the second end fitting being adapted for fluidly connecting the first end of the convoluted tube to a chromatographic column;
c) a chromatographic column adapted and configured for receiving the fluid mixture from the pre-heater assembly and adsorbing a portion thereof; and
d) an active heating source in contact with the chromatographic column for heating the fluid contained in the column;
wherein the convoluted tube of the pre-heater assembly is positioned adjacent to the active heating source such that the fluid mixture in the tube is heated thereby.

2. A chromatographic system as recited in claim 1, further comprising a thermally conductive film attached to an outer surface of the convoluted tube and adjacent to the active heating source, the film being adapted for conveying heat from the active heating source of the chromatographic column to the convoluted tube.

3. A chromatographic system as recited in claim 1, further comprising a support element for the pre-heater assembly having at least one channel formed in an exterior surface thereof and adapted for receiving the convoluted tube.

4. A passive pre-heater assembly as recited in claim 3, wherein the support element is made from aluminum.

5. A passive pre-heater assembly as recited in claim 3, wherein the support element has a U-shaped axial cross section and is adapted and configured for being inserted into a column tray.

6. A chromatographic method comprising the steps of:
   a) providing a fluid injector for supplying a fluid mixture at a desired pressure and velocity;
   b) fluidly attaching a first end of a pre-heater assembly to the injector, the pre-heater assembly adapted for receiving the fluid mixture from the fluid injector and passively providing heat thereto and including:
      i) an elongated tube having first and second ends and a fluid passage extending centrally therebetween, the tube being formed so as to have a plurality of convolutions arranged such that a successive convolution is axially offset from a previous convolution such that the plurality of convolutions stimulates secondary flows in a primary fluid flow stream; and
      ii) first and second end fittings attached respectively to the first and second ends of the tube, the first end fitting being adapted for fluidly connecting the first end of the convoluted tube to the fluid injector and the second end fitting being adapted for fluidly connecting the first end of the convoluted tube to a chromatographic column;
   c) fluidly attaching a chromatographic column to a second end of the pre-heater assembly, the column being adapted and configured for receiving the pre-heated fluid mixture from the pre-heater assembly and adsorbing a portion thereof;
   d) providing an active heating source in contact with the chromatographic column for heating the fluid contained in the column; and
   e) positioning the pre-heater assembly adjacent to the active heating source such that the fluid mixture provided to the pre-heater assembly is heated thereby.

7. A chromatographic method as recited in claim 6, further comprising the step of attaching a thermally conductive film to an outer surface of the convoluted tube and adjacent to the active heating source, the film being adapted for conveying heat from the active heating source of the chromatographic column to the convoluted tube.

8. A chromatographic method as recited in claim 6, further comprising the step of providing a support element for the pre-heater assembly having at least one channel formed in an exterior surface thereof and adapted for receiving the convoluted tube.

* * * * *